United States Patent [19]
Lahitte et al.

[11] Patent Number: 5,115,200
[45] Date of Patent: May 19, 1992

[54] METHOD AND APPARATUS FOR TESTING THE IMPEDANCE OF TWO ELECTRICALLY CONDUCTING MEMBERS USING TWO PAIRS OF ELECTRODES IN WHICH THE SPACING OF THE PAIRS IS ADJUSTABLE AND THE ELECTRODES ARE INDEPENDENTLY AXIALLY SLIDABLE

[75] Inventors: Pierre V. A. Lahitte, Salaunes; Michel J. Raymond, Listrac-Medoc; Jean-Paul Kayser, Saint-Medard-en-Jalles, all of France

[73] Assignee: Societe Nationale Industrielle Aerospatiale, Paris, France

[21] Appl. No.: 559,498

[22] Filed: Jul. 26, 1990

Related U.S. Application Data

[63] Continuation of Ser. No. 788,136, Oct. 16, 1985, abandoned.

[30] Foreign Application Priority Data

Oct. 22, 1984 [FR] France .............................. 84 16138

[51] Int. Cl.⁵ ...................... G01R 27/14; G01R 31/02
[52] U.S. Cl. .................................. 324/718; 324/691; 324/72.5
[58] Field of Search ............ 324/691, 715, 718, 72.5, 324/158 P

[56] References Cited

U.S. PATENT DOCUMENTS

| 2,142,619 | 1/1939 | Sciaky | 324/64 |
| 2,401,917 | 6/1946 | Drake | 324/64 |
| 3,466,539 | 9/1969 | Pitts et al. | 324/215 |
| 4,567,427 | 1/1986 | Hattori et al. | 324/64 |

FOREIGN PATENT DOCUMENTS

| 8801390 | 2/1988 | U.S.S.R. | 324/218 |
| 1169711 | 5/1969 | United Kingdom | 324/64 |

Primary Examiner—Walter E. Snow
Attorney, Agent, or Firm—Fisher, Christen & Sabol

[57] ABSTRACT

A process and apparatus are provided for checking the electric continuity of an electrically conducting material device, in which a current is injected between two points of said device and the resulting voltage between these points is measured. The invention is remarkable in that said current is an AC current and its pulsation is chosen sufficiently large so that the impedance between the two points, measured by the ratio of said voltage and of the current, may be considered as being equal to the product of the inductance of the path of the current between said points multiplied by said pulsation.

8 Claims, 6 Drawing Sheets

METHOD AND APPARATUS FOR TESTING THE IMPEDANCE OF TWO ELECTRICALLY CONDUCTING MEMBERS USING TWO PAIRS OF ELECTRODES IN WHICH THE SPACING OF THE PAIRS IS ADJUSTABLE AND THE ELECTRODES ARE INDEPENDENTLY AXIALLY SLIDABLE

This is a continuation of application Ser. No. 788,136, filed Oct. 16, 1985 now abandoned.

BACKGROUND OF THE INVENTION

1. Field of the Invention

The present invention relates to a method and apparatus for checking the electric continuity of a device made from an electrically conducting material by impedance measurement. Such a device may for example be formed by an assembly of metal parts or else by a monolithic conducting part likely to comprise defects.

2. Description of the Prior Art

The present invention relates to the non destructive testing of such electrically conducting devices and, more particularly, to checking the electric continuity of these devices.

As is known, particularly in the aeronautic field, it is current practice for metal assemblies to be formed by spot connections, for example by rivetting, screwing, welding or similar. Despite these connection methods, by their nature discontinuous, it is often indispensable for the assemblies obtained to provide as uniform a mechanical contact as possible between the assembled parts, so as to provide an electric continuity therebetween which is homogeneous and of low resistance. In fact, it is indispensable for the flow of electric currents passing through these assemblies to take place without privileging certain particular paths, which could generate imbalances prejudicial to the mechanical strength of said assemblies or of the devices associated therewith.

By way of first example, we may consider the action of lightning on an aircraft wing. It is known that the skin of an aircraft wing is formed from metal plates, whose edges overlap and are fixed together by rivetting. In the case where the lightning strikes such as wing, it generates lightning currents flowing therethrough. If the overlapping parts of the metal plates as a whole are not in sufficiently good mechanical contact to provide good homogeneous electric continuity, there then appear, on said wing, zones of good contact and so of low electric resistance and zones of poor contact and so of high electric resistance. The lightning currents then generate, between these zones of different values of electric resistance, electric arcs whose effects may be such as to endanger the safety of the flight of the aircraft.

Similarly, in order to protect certain electronic installations against parasites due to electromagnetic fields, said installations are enclosed in cases capable of forming sealed electromagnetic enclosures. Such cases are generally formed by assembly. Thus, if such an assembly presents a defect of electric continuity in a zone of the case, the currents induced by the parasite electromagnetic fields cannot flow through this zone and so a break in the protection in the electromagnetic enclosure occurs so that the parasites may reach the installation enclosed therein.

Thus, it is often necessary, in spot assemblies, on the one hand, to make sure that the electric continuity is practically as good as that of a monolithic piece and, on the other hand, to check the quality of the electric continuity.

It should be further noted that, for continuous assemblies, for example by welding, it may also be useful to check the quality of the electric continuity.

One of the objects of the present invention is therefore, in order to check the quality of the electric continuity of an assembly (a spot or continuous assembly), to measure the low, and even very low contact impedances existing between assembled metal parts.

A method is already known for checking the continuity of metal assemblies, in which a DC measuring current is injected between the assembled parts and the resulting DC voltage is measured therebetween. Consequently, it is possible to know the electric resistance between said parts. However, as will be shown hereafter, there exist numerous cases in which such a method cannot provide a significant measurement.

The present invention overcomes this drawback. It allows the electric resistivity and the skin effect of a monolithic conducting piece to be measured TM with the aim for example of detecting defects.

SUMMARY OF THE INVENTION

To this end, in accordance with the invention, the method for checking the electric continuity of an electrically conducting material device, in which a current is injected between two points of said device and the resulting voltage between these points is measured, is remarkable in that said current is an AC current and in that its pulsation is chosen sufficiently high for the impedance between the two points, measured with respect to said voltage and said current, to be considered as being equal to the product of the inductance of the path of the current between said points multiplied by said pulsation.

Thus, since said inductance is proportional to the length of the path of the current, said measured impedance is also proportional to this length. Measurement of the impedance therefore becomes significant of the length of the path of the current and so allows abnormally large lengths resulting from zones of poor conduction to be detected.

When the method of the invention is used for checking the electric continuity along an elongate junction between two metal parts, a plurality of successive measurements of said impedance are made at a plurality of pairs of points distributed on each side of said junction, and there along, and said measurements are compared. Thus those of these measurements differing too much from the others and indicating discontinuities of said junction are determined.

The present invention also provides an apparatus for checking the electric continuity of an electrically conducting material device, said apparatus comprising a current generator supplying a first pair of contact electrodes intended to inject a current between two points of said device, a voltmeter measuring the voltage generated between said points and taken through a second pair of contact electrodes. In accordance with the invention, this apparatus is remarkable in that it comprises computing means for working out the ratio between said voltage and said current, in that the current generator is of the AC type and in that the pulsation of the current which it generates is sufficiently large for said ratio to be considered as being equal to the product of the inductance of the path of said current between said points multiplied by said pulsation.

Preferably, each of said pairs of electrodes is formed of two coplanar electrodes and the planes of said first and second pairs of electrodes form therebetween a constant angle. Thus, the interaction between the two pairs of electrodes is constant and the error of measurement which results therefrom is also constant and so can be readily corrected.

In order to minimize this error of measurement, the planes of said first and second pairs of electrodes may be made orthogonal to each other.

However, considering the preceding remark concerning the constancy of the error, when the angle between said planes remains constant, this latter arrangement is not necessarily the most advantageous. In fact, it may be interesting for the planes of said first and second pairs of electrodes to be parallel.

This is for example the case when said first and second pairs of electrodes form a rigid portable monobloc assembly, available to an operator and connected to the rest of the apparatus by electric connections.

So as to make successive comparable measurements, it is advantageous, for each pair of electrodes, for the spacing between two electrodes to be fixed and for this spacing to be substantially the same for the two pairs of electrodes.

On the other hand, in order to facilitate positioning of the contact electrodes, it is preferable for the spacing between two couples of electrodes each comprising an electrode from each pair to be adjustable. Thus, it may be adapted to the structure of the assembly to be checked.

In order to further increase the adaptability of the electrodes to said assembly, at least one of the two couples of electrodes may advantageously slide parallel to its plane (and so to that of the other couple of electrodes).

At least one of the electrodes may be fixed with respect to said portable monobloc assembly.

Preferably, said electrodes are electromagnetically protected by the casing.

BRIEF DESCRIPTION OF THE DRAWINGS

The invention will be better understood from the Figures of the accompanying drawings. In these Figures, identical references designate similar parts.

DESCRIPTION OF THE PREFERRED EMBODIMENTS

Figure 1:
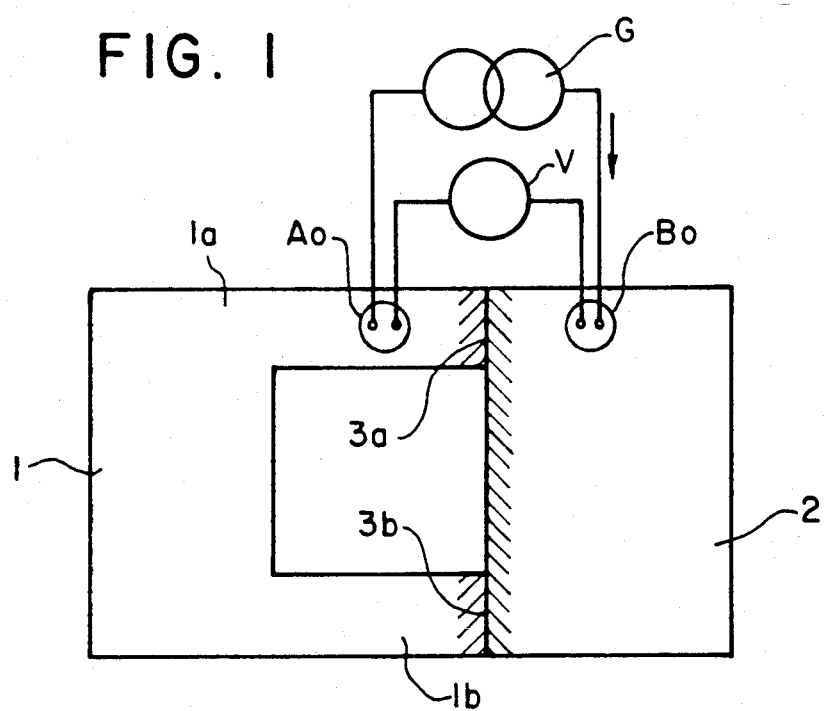
FIG. 1 is a schematical view illustrating comparatively the prior technique and the present invention.

In FIG. 1 there has been shown schematically, by way of example, a metal case 1 resting on a ground plane 2 by two feet 1a and 1b, respectively. The contact zones between each of said feet and the ground plane are designated by the references 3a and 3b.

In the prior technique, for measuring the contact resistances at zones 3a and 3b, a DC current generator G is used for injecting a DC current I between zones Ao and Bo, of parts 1 and 2, situated respectively on each side of the contact zone 3a, for example. With a DC voltage meter V, the voltage U between zones Ao and Bo is measured and the contact resistance R is determined by the ratio $_I^U$.

In the present case, it will be noted that the measured resistance R does not correspond to the contact resistance of the single zone 3a, but to the resistance resulting from the fact that the contact zones 3a and 3b are in parallel. If the contact of zone 3b is excellent so that the resistance between the zones Ao and Bo through leg 1a is of the order of $10^{-5}$ ohm, whereas the contact resistance of zone 3a is only small, giving a resistance between Ao and Bo through branch 1b, for example of the order of $10^{-3}$ ohm, DC current measurement will give the value $9.9 \times 10^{-6}$ ohm for the resulting resistance R.

If now, with the contact resistance of zone 3b remaining excellent and equal to $10^{-5}$ ohm, there is no longer any contact at 3a, the measured value R will be equal to $10 \times 10^{-6}$ ohm.

Thus, by using such a known measurement, the difference of measurement between a good contact ($10^{-3}$ ohm) and an inexistant contact is only $10 \times 10^{-6} - 9.9 \times 10^{-6} = 0.1 \times 10^{-6}$ ohm.

Such a measurement cannot then be significant.

The present invention overcomes this drawback of the known method mentioned above by using a current generator G and a voltage meter V of an AC current and no longer a DC current type.

Thus, between zones Ao and Bo, the measurement is made of an impedance $Z = _I^U$.

This impedance Z is formed, on the one hand, by the pure resistance R resulting from the quality of the contact and the conductivity of the parts in contact and, on the other hand, from an inductance L and it is equal to $$Z = \sqrt{R^2 + L^2 \times w^2} ,$$

w being the pulsation of the measuring current I.

The resistance R and the inductance L are both proportional to the length of the path of the current however, the preceding example showed that the resistance R was only slightly sensitive to this length, so that a variation of length of the path cannot be detected significantly by a variation of the term $R^2$ of Z.

On the other hand, the term $L^2w^2$ may assume a high value, by adequately choosing the pulsation w. If w is chosen sufficiently great, $L^2w^2$ becomes very great with respect to $R^2$ so that we may write:

$$Z = Lw.$$

The measured impedance Z is therefore then directly proportional to the inductance L and so the length of the path of the current.

Referring again to FIG. 1, and to the preceding example, the method of the invention will allow the poor distribution of the contact between two bearing faces 3a and 3b to be detected. In fact, the impedance of the path of the current through leg 1b will become great with respect to that of the path through leg 1a, which will appreciably reduce the disturbance produced in the measurement of the path in leg 1a.

Figure 2:
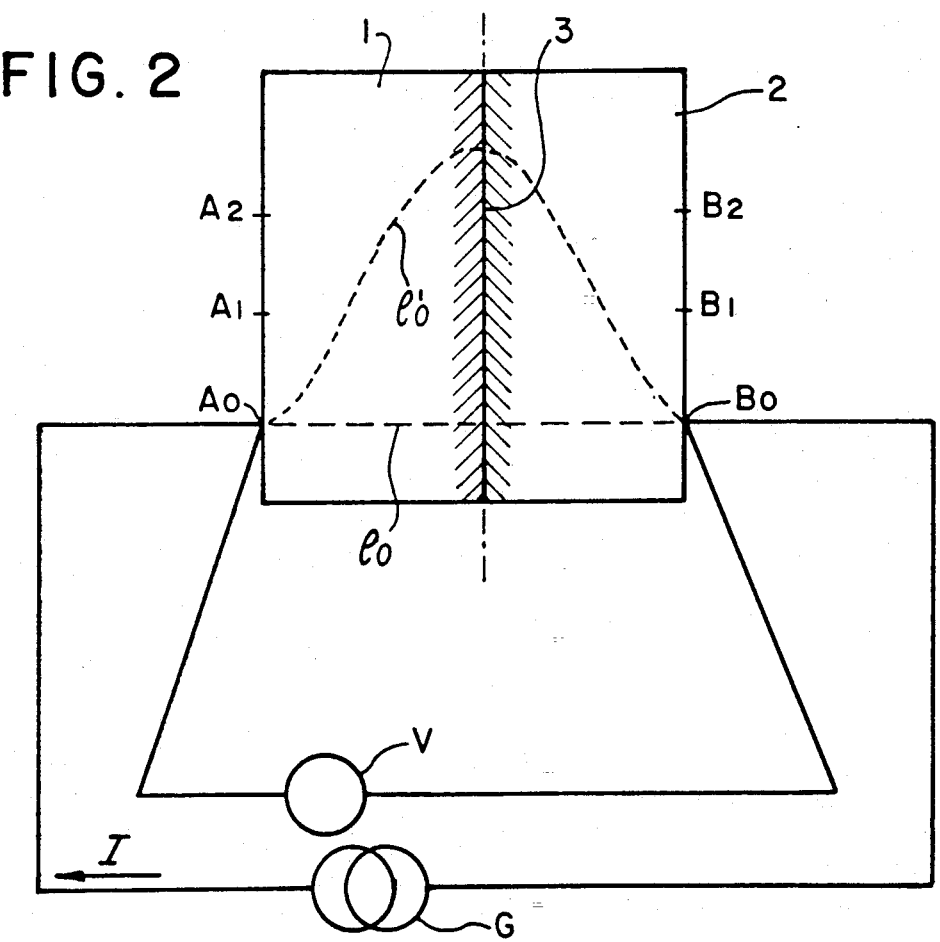
FIG. 2 gives schematically another advantageous example of application of the present invention.

In FIG. 2 have been shown two metal plates 1 and 2 assembled along a contact line 3. If a measuring current I is applied between the parts 1 and 2, on each side of the contact line 3, this current must follow a direct path lo between its points of application Ao and Bo, if the electric quality of the contact line 3 is sufficiently good.

On the other hand, if the electric quality of the contact line 3 is not good between the application points Ao and Bo, the measuring current I will follow a deviated path lo'.

With the present invention it can be detected whether the current I follows path lo or else path lo', which would not be the case with the known DC current method mentioned above, since only small resistance variations would occur in that case.

It will be readily understood that by making a series of measurements between the pairs of points Ao and Bo, then $A_1$ and $B_1$, $A_2$ and $B_2$ etc along the contact line 3, the electric quality of said line can be checked.

In accordance with the invention, successive measurements are then made at characteristic points of the assembly to be checked, and these measurements are compared with each other so as to determine the distribution of the electric continuity.

If the contact line 3 is electrically perfect, all the measurements between Ao and Bo, $A_1$ and $B_1$, $A_2$ and $B_2$, etc... must give identical results. A variation of measurement will therefore indicate an electric discontinuity of said line 3.

The same can be said when the measurements are made on a monolithic piece for detecting defects therein.

So that the impedance Z may be considered with a good approximation as being equal to $L\omega$, it is indispensable for the pulsation to be high. The frequency of the measuring current I must also therefore be high. Satisfactory results have been obtained up to 1MHz.

However, putting the method of the invention into practice requires a few precautions, since the AC measuring current produces radiation which might disturb the measurements, these disturbances being all the greater the higher the frequency of the measuring current. It is therefore necessary to provide screens and/or a particular arrangement, as shown in the example of FIG. 3.

Figure 3:
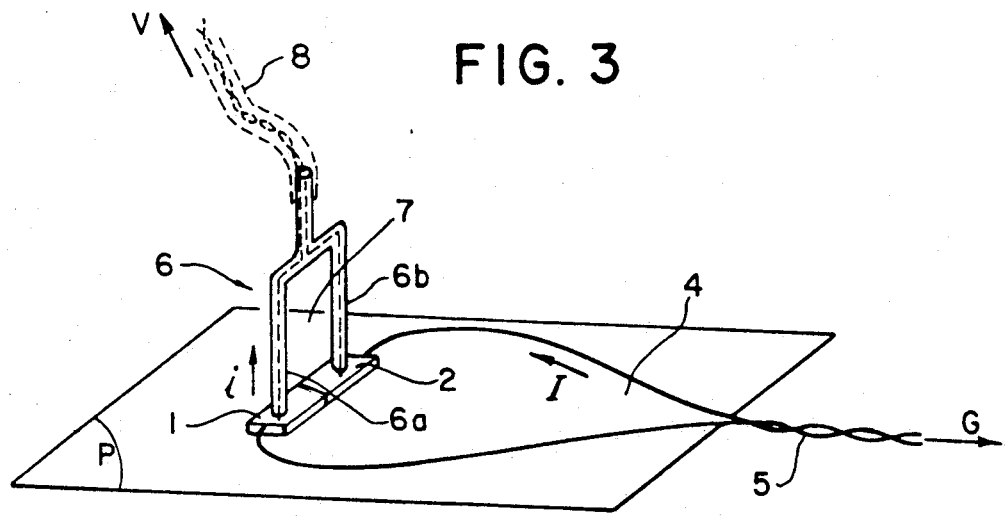
FIG. 3 illustrates one embodiment of the present invention.

In FIG. 3, the assembly to be tested 1, 2 has been shown disposed in a plane P. A loop 4 for injecting the measuring current I into the assembly 1, 2 is also disposed in plane P. This loop 4 is formed by the separation of the current injection wires 5 connected to the AC current generator G. The ends of wires 5 form contact electrodes.

In addition a measuring probe 6 has been provided having two parallel rectilinear legs 6a and 6b and forming a test loop 7. Legs 6a and 6b are respectively in contact with parts 1 and 2 and each comprise a wire 8. Wires 8 are brought together outside probe 6 and connect this latter to voltmeter V. The ends of wires 8 form contact electrodes on assembly 1, 2.

The current i flowing through the test loop 7 is very small with respect to the current I flowing through the injection loop 4, in the case where the assembly 1, 2 has a low impedance. Consequently, the test loop 7 risks being strongly coupled to the injection loop 4.

To overcome this drawback, in the apparatus of FIG. 3,

- the plane of the test loop 7 is disposed orthogonally to the plane of the injection loop 4;
- legs 6a and 6b of the test probe 6 are disposed perpendicularly to the plane of the injection loop 4;
- the conductors 8 inside legs 6a and 6b are screened, only the bare end of these conductors projecting therefrom opposite the assembly 1, 2 for a pressure contact with said parts 1 and 2;
- legs 6a and 6b of sufficient length are provided so as to avoid any residual coupling;
- the test probe 6 is constructed in a form which is rigid indeformable under the effect of the pressure exerted by the operator on the ends of conductors 8 when they are placed in contact with the assembly 1, 2 to be tested.

Figure 4:
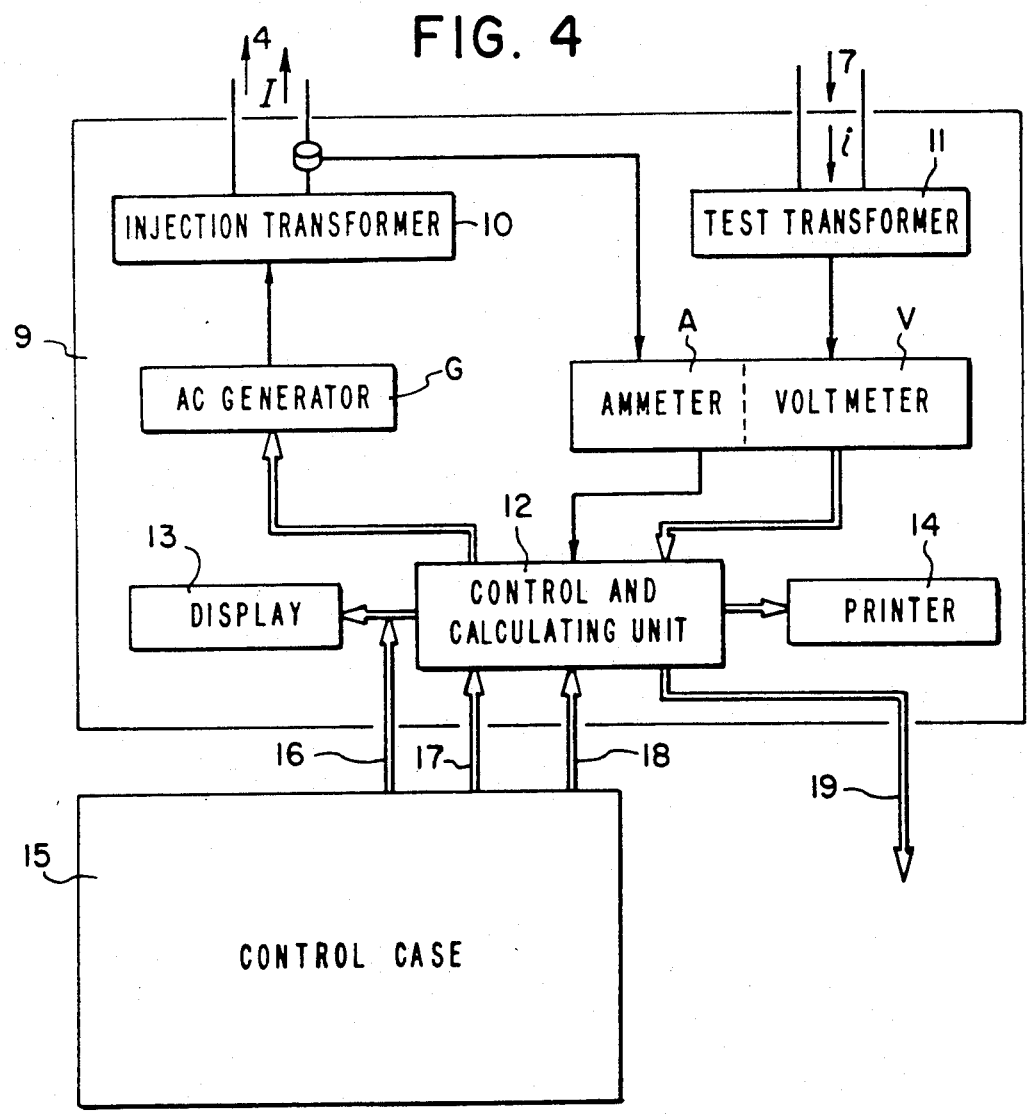
FIG. 4 shows the block diagram of the electric circuit of the apparatus of the invention.

As shown in FIG. 4, the testing apparatus of the invention may comprise, in addition to the injection and test loops 4 and 7, a case 9 inside which are disposed the AC current generator G and the voltmeter V, as well as an ammeter . Generator G feeds the injection loop 4 through an injection transformer 10, at the output of which the injection current I is measured by the ammeter A. The test loop 7 is connected to voltmeter V through a test transformer 11.

A control and calculating unit 12 controls the generator G, receives the measurements I and U respectively of A and V, drives a display unit 13 and a printer 14, is in connection through connections 16, 17 and 18 with the control case 15 available to &he operator and may be connected to a centralized system through a connection 19.

Generator G is for example capable of supplying a current of 100mA whose frequency may vary from 10KHz to 1MHz. The control and calculating unit 12 ensures automation of the operation of the assembly and works out the calculation of $i^U$ Transformers 10 and 11 provide the galvanic insulation between case 9 and loops 4 and 7.

Case 9 which contains the elements 10, 11, 12, 13, 14, the generator G, the voltmeter V and ammeter A is for example in the form of a standardized rack unit.

The control case 15 is separated from case 9; it is portable and available to the operator who thus has access to the measuring apparatus 9.

Preferably, the injection loop 4 and the test or measuring loop 7 are both in the form of probes, handled by said operator (in FIG. 3, only the test loop 7 is shown in the form of a probe 6). These test and injection probes are then, as case 15, physically separated from case 9, but in electric connection therewith.

In FIG. 3 the test loop 7 has been shown disposed orthogonally to the injection loop 4. This arrangement corresponds to the minimum of coupling between said loops. However, calculation shows that if said loops are not orthogonal and if consequently the electromagnetic coupling therebetween is not minimum, the error of measurement caused by such electromagnetic coupling is constant if the angle between the planes of the injection and test loops is constant.

Thus, more especially so as to be able to form a monobloc assembly comprising combined injection probe and test probe, it may be advantageous to dispose said test and injection probes so that their planes form an angle differing from 90°. It is insufficient, when using the results, to take into account the specific error generated by the chosen geometry. To take this specific error into account, it is possible to calibrate the device by means of a plurality of samples 1, 2 of known electric characteristics.

Figure 5:
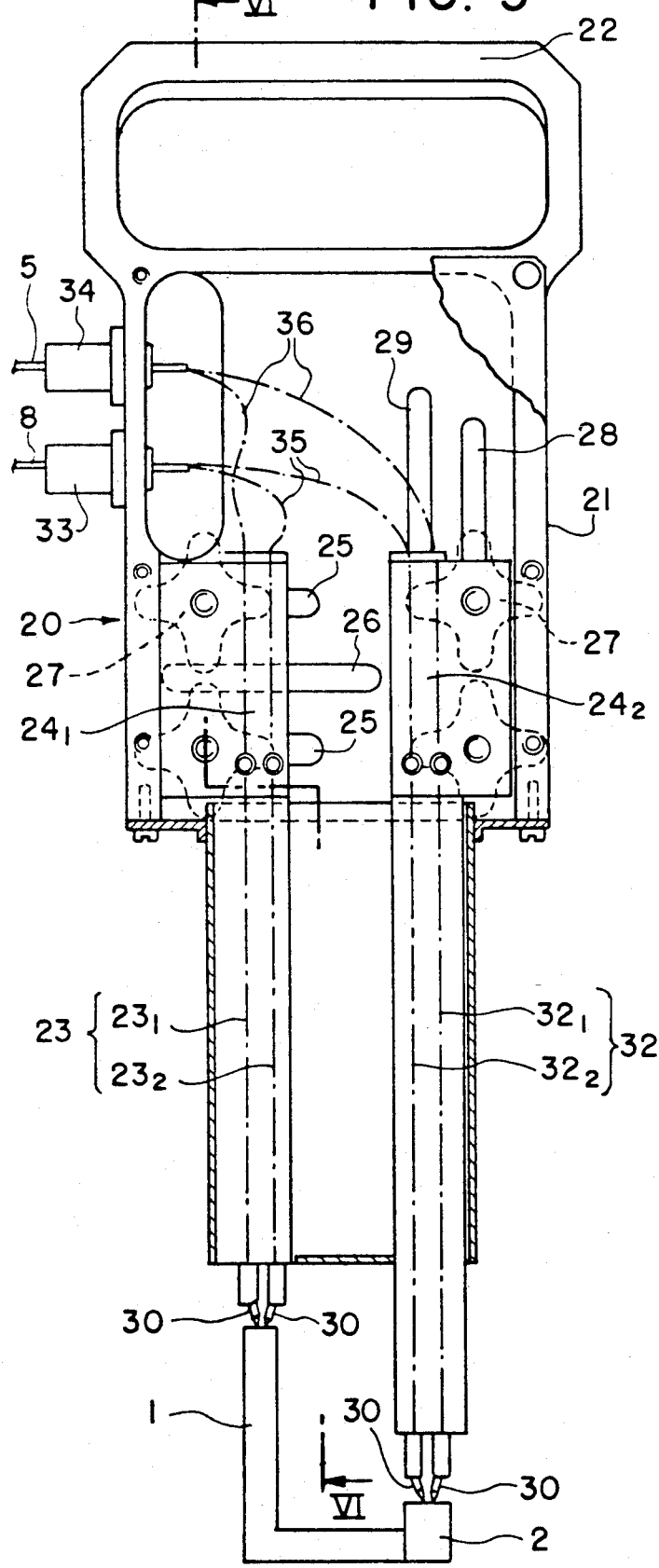
FIG. 5 is a front elevational view, with parts cut away of one embodiment of an electrode holder assembly for the apparatus of the invention.
Figure 6:
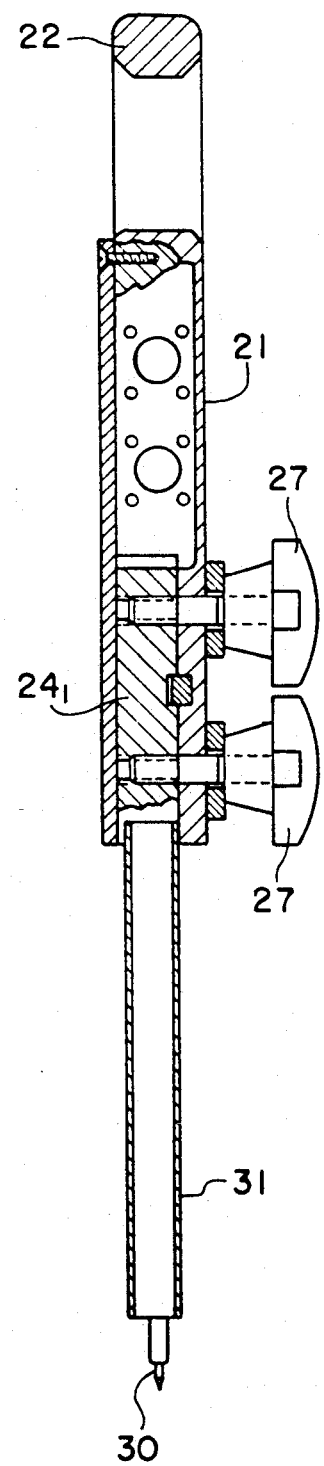
FIG. 6 is a section through line VII—VII of FIG. 5.
Figure 7:
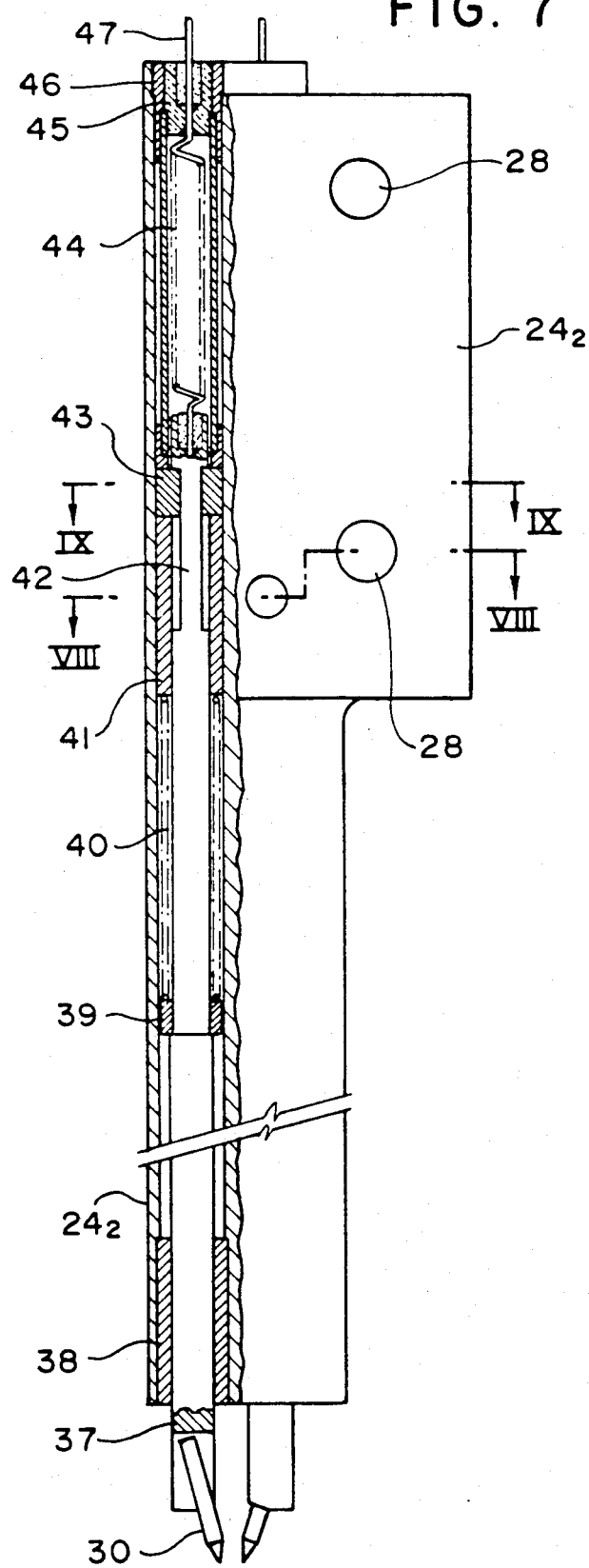
FIG. 7 is a side elevational view, in partial longitudinal section, of the right hand electrode holder block of the assembly shown in FIG. 5.
Figure 11:
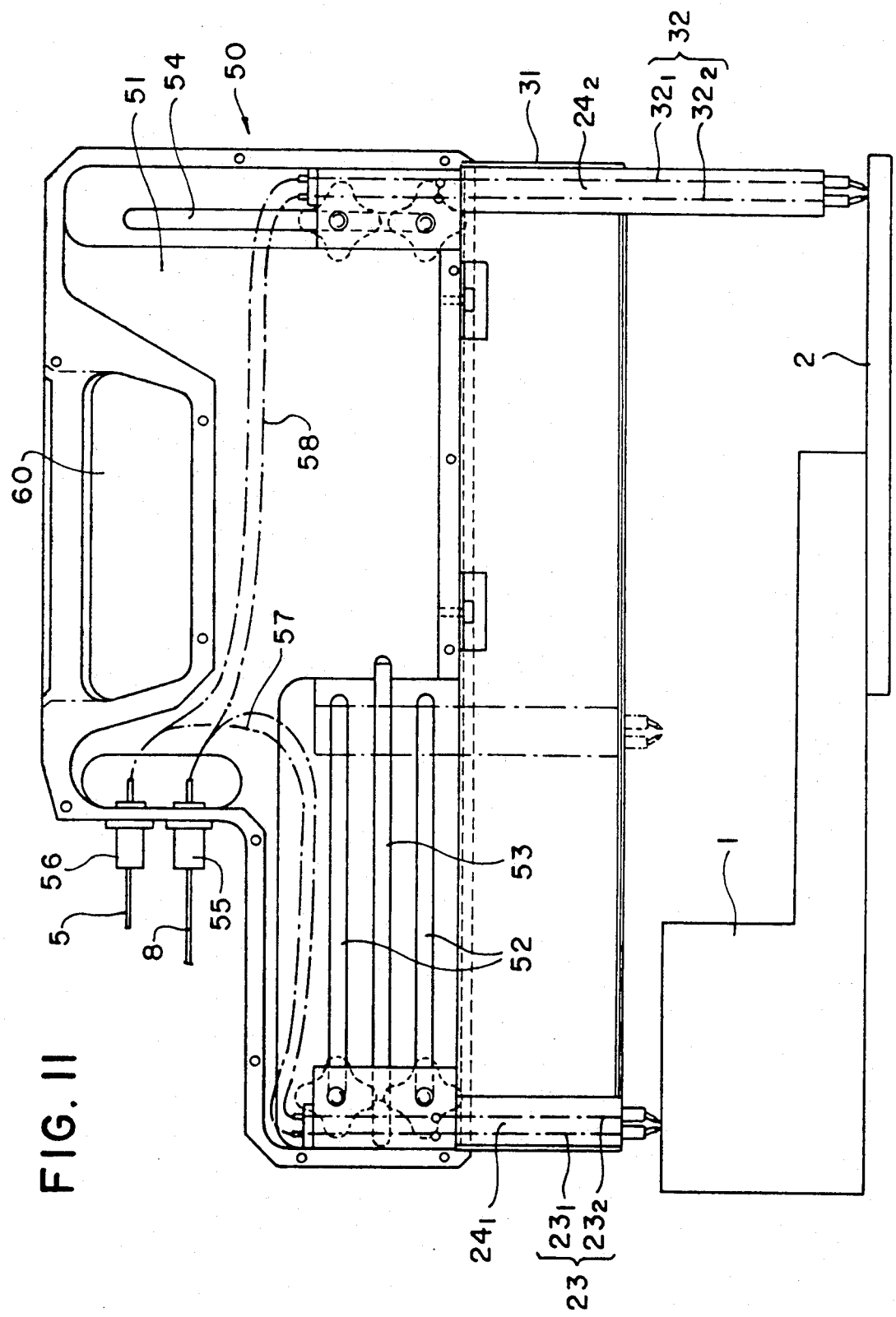
FIG. 11 illustrates in elevation a variant of the electrode holder block for the apparatus of the invention.

In FIGS. 5 and 11 have been shown two embodiments of such a monobloc probe assembly, in which the injection and test loops are coplanar.

The embodiment 20 of FIGS. 5 to 10 comprises a body 21 having a handle 22 and comprising a first couple of electrodes 23 and a second couple of electrodes 32.

Each couple of electrodes 23 and 32 is formed of an injection loop electrode and a test loop electrode, said injection loop comprising the pair of electrodes $23_1$, said test loop comprises the pair of electrodes $32_1$ whereas said test loop comprises the pair of electrodes $23_2$, $32_2$.

The pair of electrodes $23_1$, $32_1$ and the pair of electrodes $23_2$, $32_2$ are connected respectively electrically to wires 5 and wires 8 through conductors 36 and 35 and connectors 34 and 33.

The two electrodes of each couple are fixed to a block $24_1$ or $24_2$, providing a fixed distance between the axes of said electrodes.

Each electrode $23_1$, $23_2$, $32_1$, $32_2$ is formed from a sliding metal rod 37, mounted in block $24_1$ or $24_2$ by a socket system 38, 39, 41 and 46. Springs 40 and 44 ensure for each electrode a longitudinal contact elasticity; in addition, springs 44 ensure the constant length of the circuits. A flat portion 42 cooperating with a ring 43 permits orientation of the probe tip 30.

Figure 10:
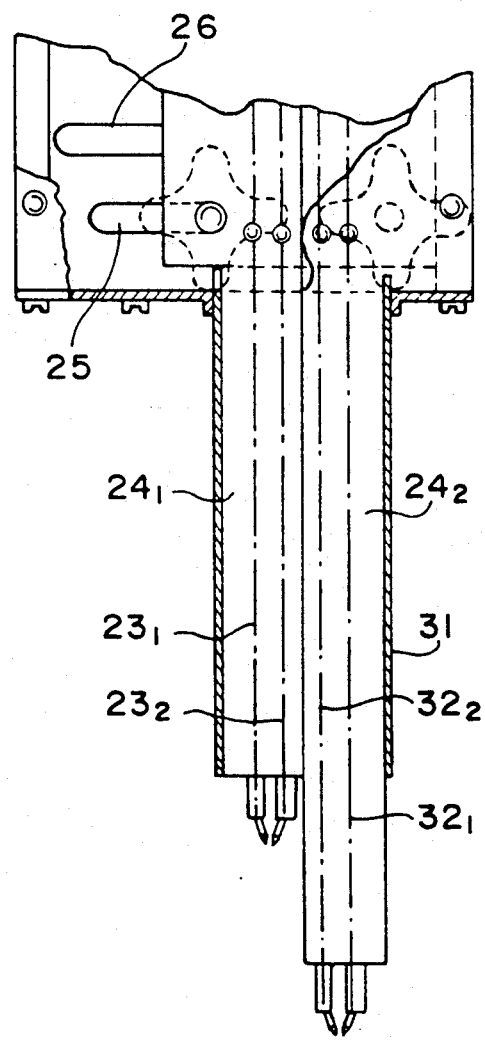
FIG. 10 is a partial view of the lower part of the block of FIG. 5, the electrodes being in the closed up position.
Figure 8:
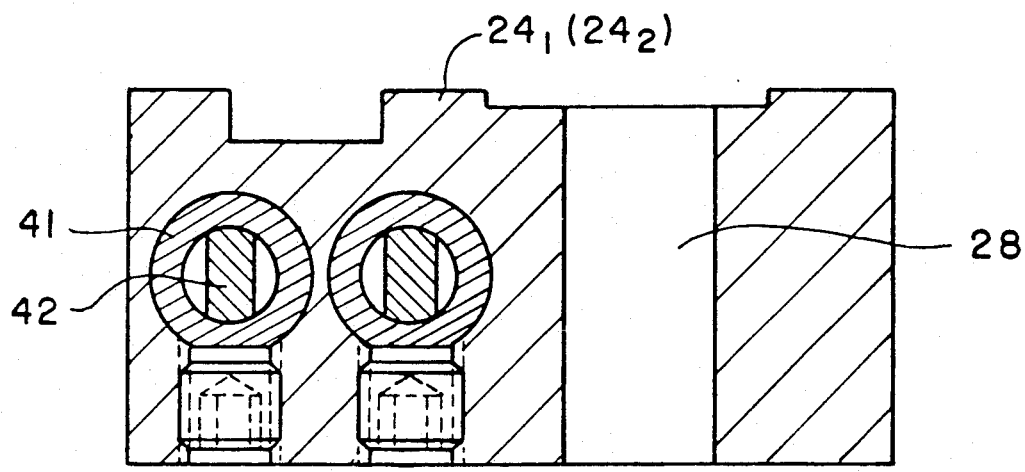
FIGS. 8 and 9 are sections respectively through lines VIII—VIII and IX—IX of FIG. 7.
Figure 9:
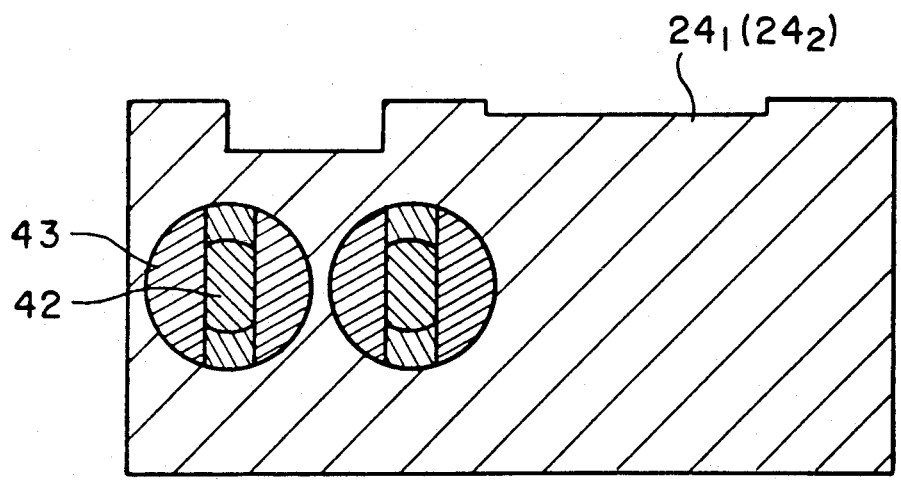

An insulating plug 45 allows the end 47 of spring 44 to pass sealingly therethrough. In FIG. 10, the couples of electrodes 33 and 32 have been shown in the extreme closed up position. A casing 31 protects the couples of electrodes 23 and 32 electromagnetically.

In a variant 50 shown in FIG. 11, we find again electrodes 23 and 32 mounted for sliding with respect to body 51, having a handle 60. Grooves 52, 53, 54 allow the arrangement of said couples of electrodes to be adjusted which will be connected together in pairs $23_1$, $32_1$ and $23_2$, $32_2$ to the terminals 56 and 55 by conductors 57 and 58.

The device 50 is in a form allowing a greater adjustment range for spacing the electrodes than device 20.

For the examples which have been described, the four electrodes are slidable so as to be adaptable to the unevenesses of the bearing surfaces on the assemblies to be tested, and on the other hand so that the operator is not compelled to search manually for a stable position in which the probes might be in contact. It will be readily understood that in theory the four probes (30) could be fixed but at least two of them must be mobile. In fact, it is very easy to engage one fixed probe then a second fixed probe but, with this balance achieved, the other probes must lend themselves to the form of contact. Thus, the examples described are not limitative of the devices which may be constructed.

What is claimed is:

1. An apparatus for determining the quality of an elongate electrical junction between two electrically conducting members, wherein said apparatus comprises:
   a) a generator for producing an alternating current having a frequency of 10KHz to 1MHz;
   b) a voltmeter;
   c) an ammeter operatively connected to said generator;
   d) an impedance calculating means; and
   e) a body having a first pair of spaced-apart parallel rectilinear electrodes extending from said body, said first pair of electrodes being operatively connected to said generator, a second pair of spaced-apart parallel electrodes extending from the body and closely-spaced to said first pair of electrodes, a first electrode of said first pair of electrodes and a first electrode of said second pair of electrodes being independently axially slidable within a first socket cooperating with said body, and a second electrode of said first pair of electrodes and a second electrode of said second pair of electrodes being independently axially slidable within a second socket socket cooperating with said body, at least one of said first and second socket being movable on said body for selectively adjusting the spacing between each electrode of said first and second pair of electrodes, each electrode further being independently biased by a complementary spring member to urge said electrode outwardly from said body, stop means for limiting outward displacement of each electrode, each of said spring members biasing said first pair of electrodes having a first end electrically connected to said electrode and a second end electrically connected to said generator, and wherein said spring members biasing said second pair of electrodes have a first end electrically connected to each electrode of said second pair of electrodes and a second end electrically connected to said volunteer, wherein said first pair of electrodes and spring members in cooperation with said generator, ammeter and electrically conducting members define a first electrical loop for injecting an alternating electric current across said electrical junction and wherein said second pair of electrodes and complementary spring members in cooperation with said voltmeter and said electrically conducting members define a second electrical loop substantially the same length at the first loop to measure the voltage drop across said junction;
   wherein said impedance calculating means is operatively connected to said voltmeter and is operatively connected to said generator to calculate impedance across said junction.

2. The apparatus of claim 1 wherein said electrodes have a tip angled with respect to a longitudinal axis of said electrodes.

3. The apparatus of claim 1 including means to selectively adjust the spacing between each electrode of said first and second pair of electrodes.

4. The apparatus of claim 1 wherein each of said electrodes are electromagnetically shielded.

5. A method for determining electrical continuity and quality of a weld along an elongate welded junction between two electrically conducting members, comprising:
   a) injecting an alternating electric current having a frequency between 10KHz and 1MHz between two points disposed on each side of said junction and measuring the AC voltage between said points with impedance measuring means comprising a body having a first pair of spaced-apart parallel rectilinear electrodes extending from said body, said first pair of electrodes being operatively connected to an alternating current generator, a second pair of spaced-apart parallel electrodes extending from the body and closely-spaced to said first pair of electrodes, a first electrode of said first pair of electrodes and a first electrode of said second pair of electrodes being independently axially slidable within a first socket cooperating with said body, and the other electrode of said first pair of electrodes and the other electrode of said second pair of electrodes being independently axially slidable within a second socket cooperating with said body, at least one of said first and second socket being movable on said body for selectively adjusting the spacing between each electrode of said first and second pair of electrodes, each electrode further being independently biased by a complementary spring member to urge said electrode outwardly from said body, stop means for limiting outward displacement of each electrode, each of said spring members biasing said first pair of electrodes having a first end electrically connected to said electrode and a second end electrically connected to a generator, each of said spring members biasing said second pair of electrodes having a first end electrically connected to each electrode of said second pair of electrodes and a second end electrically connected to a voltmeter, wherein said pair of electrodes and complementary spring members in cooperation with said generator and electrically conducting members define a first electrical loop for injecting said current, and wherein said second pair of electrodes and spring members in cooperation with said voltmeter and said electrically conducting members define a second electrical loop substantially the same length as the first loop for measuring a voltage across said junction;

b) measuring the voltage drop and calculating the impedance across said junction wherein said impedance is proportional to the electrical path between said points, c) repeating steps a) and b) in at least two additional points disposed along each side of said junction to obtain at least two additional impedance measurements, e) comparing the calculated impedance measurements thereby determining any discontinuity and the electric continuity along said junction.

6. The apparatus of claim 1, wherein at least one of said first and second socket is movable on said body axially with respect to said electrodes for selectively adjusting the extension of the electrodes out of said body.

7. A method for determining electrical continuity along an elongate junction between two electrically conducting members, with means comprising a body having a first pair of spaced-apart parallel rectilinear electrodes extending from said body, aid first pair of electrodes being operatively connected to a generator, a second pair of spaced-apart parallel electrodes extending from the body and closely-spaced to said first pair of electrodes, a first electrode of said first pair of electrodes and a first electrode of said second pair of electrodes supported by and being independently axially slidable within a first socket cooperating with said body, and a second electrode of said first pair of electrodes and a second electrode of said second pair of electrodes being independently axially slidable within a second socket cooperating with said body, at least one of said first and second socket being movable on said body for selectively adjusting the spacing between each electrode of said first and second pair of electrodes, each electrode further being independently biased by a complementary spring member to urge said electrode outwardly from said body, stop means for limiting outward displacement of each electrode, each of said spring members biasing said first pair of electrodes having a first end electrically connected to said electrode and a second end electrically connected to said generator, each of said spring members biasing said second pair of electrodes having a first end connected to each electrode of said second pair of electrodes and a second end electrically connected to a voltmeter, wherein said first pair of electrodes and complementary spring members in cooperation with said generator and electrically conducting members define a first electrical loop for injecting a current, and wherein said second pair of electrodes and spring members in cooperation with said voltmeter and said electrically conducting members define a second electrical loop substantially the same length as the first loop for measuring a voltage drop across said junction, said method comprising the steps of:

a) placing said means whereby said first electrodes of said first and second pair of electrodes contact a first point disposed on one side of said junction and said second electrodes of said first and second pair of electrodes contact a second point disposed on the other side of said junction;

b) injecting an alternating electric current having a frequency between 10KHz and 1MHz between said two points disposed on each side of said junction through said first pair of electrodes and measuring the AC voltage between said points through said second pair of electrodes;

c) measuring the voltage drop and calculating the impedance across said junction between said points;

d) repeating steps a), b) and c) in at least two additional points disposed along each side of said junction to obtain at least two additional impedance measurements;

e) comparing the calculated impedance measurements thereby determining any discontinuity and the electric continuity along said junction.

8. A method for determining electrical continuity along an elongate junction between two electrically conducting members, with means comprising a body having a first pair of spaced-apart parallel rectilinear electrodes extending from said body, said first pair of electrodes being operatively connected to a generator, a second pair of spaced-apart parallel electrodes extending from the body and closely-spaced to said first pair of electrodes, a first electrode of said first pair of electrodes and a first electrode of said second pair of electrodes being independently axially slidable within a first socket cooperating with said body, and a second electrode of said first pair of electrodes and a second electrode of said second pair of electrodes being independently axially slidable within a second socket cooperating with said body, said first socket being movable on said body for selectively adjusting the spacing between each electrode of said first and second pair of electrodes, and said second socket being movable on said body for selectively adjusting the extension of the corresponding electrodes of said first and second pair of electrodes out of said body, each electrode further being independently biased by a complementary spring member to urge said electrode outwardly from said body, stop means for limiting outward displacement of each electrode each of said spring members biasing said first pair of electrodes having a first end electrically connected to said electrode and a second end electrically connected to said generator, each of said spring members biasing said second pair of electrodes having a first end connected to each electrode of said second pair of electrodes and a second end electrically connected to a voltmeter, wherein said first pair of electrodes and complementary spring members in cooperation with said generator and electrically conducting members define a first electrical loop for injecting an alternating current, and wherein said second pair of electrodes and spring members in cooperation with said voltmeter and said electrically conducting members define a second electrical loop substantially the same length as the first loop for measuring a voltage drop across said junction, said method comprising the steps of:

a) placing said means whereby said first electrodes of said first and second pair of electrodes contact a first point disposed on one side of said junction and said second electrodes of said first and second pair of electrodes contact a point disposed on the other side of said junction;

b) injecting an alternating electric current having a frequency between 10KHz and 1MHz between said two points disposed on each side of said junction and measuring the AC voltage between said to points;

c) measuring the voltage drop and calculating the impedance across said junction;

d) repeating steps a), b) and c) in at least two additional points disposed along each side of said junction to obtain at least two additional impedance measurements;

e) comparing the calculated impedance measurements thereby determining any discontinuity and the electric continuity along said junction.

* * * * *